US006777194B1

(12) United States Patent
Gerdes et al.

(10) Patent No.: US 6,777,194 B1
(45) Date of Patent: Aug. 17, 2004

(54) MONOCLONAL ANTIBODIES AGAINST HUMAN PROTEIN MCM3, PROCESS FOR THEIR PRODUCTION, AND THEIR USE

(75) Inventors: Johannes Gerdes, Feldhorst (DE); Thomas Scholzen, Neritz (DE); Elmar Endi, Hamburg (DE); Claudia Wohlenberg, Hamburg (DE); Bettina Baron-Lühr, Bad Segeberg (DE); Margrit Kernbach Hahn, Kaltenkirchen (DE); Patricia Prilla, Borstal (DE); Johanna Suwinski, Wiemersdorf (DE); Rolf Knippers, Konstanz (DE)

(73) Assignee: Dakocytomation Denmark A/S, Glostrup (DK)

(*) Notice: Subject to any disclaimer, the term of this patent is extended or adjusted under 35 U.S.C. 154(b) by 0 days.

(21) Appl. No.: 09/937,649

(22) PCT Filed: Mar. 31, 2000

(86) PCT No.: PCT/EP00/02910

§ 371 (c)(1),
(2), (4) Date: Jan. 28, 2002

(87) PCT Pub. No.: WO00/59943

PCT Pub. Date: Oct. 12, 2000

(30) Foreign Application Priority Data

Apr. 1, 1999 (DE) .......................... 199 15 057

(51) Int. Cl.[7] ................... G01N 33/574; G01N 33/531; G01N 33/53; C12N 5/20; C07K 16/30
(52) U.S. Cl. ..................... 435/7.23; 435/7.95; 435/326; 435/975; 530/388.8
(58) Field of Search ........................ 530/387.1, 388.1, 530/388.8; 435/975, 7.1, 7.95, 7.23, 64, 326

(56) References Cited

U.S. PATENT DOCUMENTS

| | | | |
|---|---|---|---|
| 4,281,061 A | * | 7/1981 | Zuk et al. |
| 4,816,567 A | | 3/1989 | Cabilly et al. .............. 530/387 |
| 5,223,409 A | | 6/1993 | Ladner et al. .............. 435/69.7 |
| 5,225,539 A | | 7/1993 | Winter ..................... 530/387.3 |
| 5,876,438 A | * | 3/1999 | Kelleher et al. |
| 6,156,500 A | * | 12/2000 | Falb |
| 6,303,323 B1 | | 10/2001 | Laskey et al. |
| 6,316,208 B1 | * | 11/2001 | Roberts et al. |
| 2003/0143646 A1 | | 7/2003 | Laskey et al. |

FOREIGN PATENT DOCUMENTS

| | | |
|---|---|---|
| EP | 0125023 | 11/1984 |
| EP | 0171496 | 2/1986 |
| EP | 0173494 | 3/1986 |
| EP | 0184187 | 6/1986 |
| WO | WO 86/01533 | 3/1986 |
| WO | WO 87/02671 | 5/1987 |
| WO | WO 90/02809 | 3/1990 |
| WO | WO 91/17271 | 11/1991 |
| WO | WO 92/01047 | 1/1992 |
| WO | WO 92/010147 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |

OTHER PUBLICATIONS

Harlow E, Lane D., Antibodies a laboratory manual. Cold Spring Harbor, New York: Cold Spring Harbor Laboratory Press, 1988.*

Abaza MS, Atassi MZ. Effects of amino acid substitutions outside an antigenic site on protein binding to monoclonal antibodies of predetermined specificity obtained by peptide immunization: . . . J Protein Chem. 11(6):687–98, 1992.*

Colman PM. Effects of amino acid sequence changes on antibody–antigen interactions. Res Immunol. 145(1):33–36, 1994.*

Lederman S, et al. A single amino acid substitution in a common African allele of the CD4 molecule ablates binding of the monoclonal antibody, OKT4. Mol Immunol. 28(11):1171–81, 1991.*

Ngo J.T, Marks J., Karplus M., Computational complexity, protein structure prediction, and The Levinthal paradox in the Protein Folding Problem, ch. 14, pp. 435–508, Birkhauser, 1994.*

Tsuruga H, Yabuta N, Hashizume K, Ikeda M, Endo Y, Nojima H. Expression, nuclear localization and interactions of human MCM/P1 proteins. Biochem Biophys Res Commun. Jul. 9, 1997;236(1):118–25.*

Shaw, D.R. et al., "Mouse/Human Chimeric Antibodies to a Tumor–Associated Antigen: Biologic Activity of the Four Human IgG Subclasses," *Journal of the National Cancer Institute*, 80(19):1553–1559 (1988). (Corrected).

(List continued on next page.)

*Primary Examiner*—Christina Chan
*Assistant Examiner*—Maher Haddad
(74) *Attorney, Agent, or Firm*—Hamilton, Brook, Smith & Reynolds, P.C.

(57) ABSTRACT

The present invention relates to monoclonal antibodies against the human Mcm3 protein, hybridoma cell lines that produce such antibodies, procedures for the production and their use, pharmaceutical compositions comprising a monoclonal antibody according to the present invention, their use for the prevention and treating of certain diseases as well as methods relating to the prevention and treatment of diseases associated with Mcm3 expression. Monoclonal antibodies according to the invention detect and bind human Mcm3 monospecifically both in immunohistological and immunobiochemical detection systems. The process for the production of these monoclonal antibodies comprises an initial screening of excess hybridoma supernatant with immunobiochemical methods followed by a second screening of positive hybridoma by means of an immunohistochemical method.

27 Claims, No Drawings

OTHER PUBLICATIONS

Regenmortel, M.H.V.V. et al., "Synthetic Polypeptides as Antigens," Elsevier Science Publishers B.V., pp. 4–9 (1988).

BD PharMingen, Research Products Catalog (2000), p. 884.

Gerdes J. et al., "Production of a Mouse Monoclonal Antibody Reactive with a Human Nuclear Antigen Associated with Cell Proliferation," *Int. J. Cancer*, 31:13–20 (1983).

Baisch, H. and Gerdes, J., "Simultaneous Staining of Exponentially Growing Versus Plateau Phase Cells with the Proliferation–Associated Antibody Ki–67 and Propidium Iodide: Analysis by Flow Cytometry," *Cell Tissue Kinet.*, 20:387–391 (1987).

Maine, G.T. et al., "Mutants of S. Cerevisiae Defective in the Maintenance of Minichromosomes," *Genetics*, 106:365–385 (1984).

Blow, J.J. and Laskey, R.A., "A Role for the Nuclear Envelope in Controlling DNA Replication Within the Cell Cycle," *Nature*, 332:546–548 (1988).

Richter, A. and Knippers, R., "High–Molecular–Mass Complexes of Human Minichromosome–Maintenance Proteins in Mitotic Cells," *Eur. J. Biochem.*, 247:136–141 (1997).

Thömmes, P. et al., "Properties of the Nuclear P1 Protein, a Mammalian Homologue of the Yeast Mcm3 Replication Protein," *Nucleic Acids Research*, 20(5):1069–1074 (1992).

Hu, B. et al., "The P1 Family: A New Class of Nuclear Mammalian Proteins Related to the Yeast Mcm Replication Process," *Nucleic Acids Research*, 21(22):5289–5293 (1993).

Köhler, G. and Kilstein, C., "Continuous Cultures of Fused Cells Secreting Antibody of Predelined Specificity," *Nature*, 256:495–497 (1975).

Brown, J.P. et al., "Structural Characterization of Human Melanoma–Associated Antigen p97 with Monoclonal Antibodies," *The Journal of Immunology*, 127(2):539–546 (1981).

Brown, J.P. et al., "Protein Antigens of Normal and Melignant Human Cells Identified by Immunoprecipitation with Monoclonal Antibodies," *The Journal of Biological Chemistry*, 255(11):4980–4983 (1980).

Yeh, M.Y. et al., "Cell Surface Antigens of Human Melanoma Identified by Monoclonal Antibody," *Proc. Natl. Acad. Sci. USA*, 76(6):2927–2931 (1979).

Yeh, M.Y. et al., "A Cell–Surface Antigen Which is Present in the Ganglioside Fraction and Shared by Human Melanomas," *Int. J. Cancer*, 29:269–275 (1982).

Kozbor, D. and Roder, J.C., "The Production of Monoclonal Antibodies from Human Lymphocytes," *Immunology Today*, 4(3):72–79 (1983).

Cole, S.P.C. et al., "The EBV–Hybridoma Technique and its Application to Human Lung Cancer," *Monoclonal Antibodies and Cancer Therapy*, pp. 77–96 (1985).

Lerner, E.A., "How to Make a Hybridoma," *The Yale Journal of Biology and Medicine*, 54:387–402 (1981).

Gefter, M.L. et al., "A Simple Method for Polyethylene Glycol–Promoted Hybridization of Mouse Myeloma Cells," *Somatic Cell Genetics*, 3(2):231–236 (1977).

Galfre, G. et al., "Antibodies to Major Histocompatibility Antigens Produced by Hybrid Cell Lines," *Nature*, 266:550–552 (1977).

Fuchs, P. et al., "Targeting Recombinant Antibodies to the Surface of *Escherichia coli*:Fusion to a Peptidoglycan Associated Lipoprotein," *Bio/Technology*, 9:1369–1372 (1991).

Hay, B.N. et al., "Bacteriophage Cloning and *Escherichia coli* Expression of a Human IgM Fab," *Hum. Antibod. Hybridomas*, 3:81–85 (1992).

Huse, W.D. et al., "Generation of a Large Combinatorial Library of the Immunoglobulin Repertoire in Phage Lambda," *Science*, 246:1275–1281 (1989).

Griffiths, A.D. et al., "Human Anti–Self Antibodies with High Specificity from Phage Display Libraries," *The EMBO Journal*, 12(2):725–734 (1993).

Hawkins, R.E. et al., "Selection of Phage Antibodies by Binding Affinity," *J. Mol. Biol.*, 226:889–896 (1992).

Clackson, T. et al., "Making Antibody Fragments Using Phage Display Libraries," *Nature*, 352:624–628 (1991).

Gram, H. et al., "In Vitro Selection and Affinity Maturation of Antibodies from a Naive Combinatorial Immunoglobulin Library," *Proc. Natl. Acad. Sci. USA*, 89:3576–3580 (1992).

Garrard, L.J. et al., "F, Assembly and Enrichment in a Monovalent Phage Display System," *Bio/Technology*, 9:1373–1377 (1991).

Hoogenboom, H.R. et al., "Multi–subunit Proteins on the Surface of Filamentous Phage: Methodologies for Displaying Antibody (Fab) Heavy and Light Chains," *Nucleic Acids Research*, 19(15):4133–4137 (1991).

Barbas, C.F. et al., "Assembly of Combinatorial Antibody Libraries on Phage Surfaces: The Gene III Site," *Proc. Natl. Acad. Sci. USA*, 88:7978–7982 (1991).

Better, M. et al., "*Escherichia coli* Secretion of an Active Chimeric Antibody Fragment," *Science*, 240:1041–1043 (1988).

Liu, A.Y. et al., "Chimeric Mouse–Human IgG1 Antibody that can Mediate Lysis of Cancer Cells," *Proc. Natl. Acad. Sci. USA*, 84:3439–3443 (1987).

Liu, A.Y. et al., "Production of a Mouse–Human Chimeric Monoclonal Antibody to CD20 with Potent Fc–Dependent Biologic Activity," *The Journal of Immunology*, 139(10):3521–3526 (1987).

Sun, L.K. et al., "Chimeric Antibody with Human Constant Regions and Mouse Variable Regions Directed Against Carcinoma–Associated Antigen 17–1A," *Proc. Acad. Sci. USA*, 84:214–218 (1987).

Nishimura, Y. et al., "Recombinant Human–Mouse Chimeric Monoclonal Antibody Specific for Common Acute Lymphocytic Leukemia Antigen," *Cancer Research*, 47:999–1005 (1997).

Wood, C.R. et al., "The Synthesis and In Vivo Assembly of Functional Antibodies in Yeast," *Nature*, 314:446–449 (1985).

Shaw, D.R. et al., "Mouse/Human Chimeric Antibodies to a Tumor Associated Antigen: Biologic Activity of the Four Human IgG Subclasses," *Journal of the National Cancer Institute*, 80(19):153–159 (1988).

Morrison, S.L., "Transfectomas Provide Novel Chimeric Antibodies," *Science*, 329:1202–1207 (1985).

Di, V.T. et al., "Chimeric Antibodies," *BioTechniques*, 4(3):214–221 (1986).

Jones, P.T. et al., "Replacing the Complementarity–Determining Regions in a Human Antibody with those from a Mouse," *Nature*, 321:522–525 (1966).

Verhoeyen, M. et al., "Reshaping Human Antibodies: Grafting an Antilysczyme Activity," *Science*, 239:1534–1536 (1988).

Beidler, C.B. et al., "Cloning and High Level Expression of a Chimeric Antibody with Specificity for Human Carcinoembryonic Antigen," *The Journal of Immunology*, 141(11):4053–4060 (1988).

Mashal, R.D. et al., "Expression of Cell Cycle–regulated Proteins in Prostate Cancer," *Cancer Research*, 56:4159–4163 (1996).

Toyoshima, H. et al., "p27, a Novel Inhibitor of G1 Cyclin Cdk Protein Kinase Activity, is Related to p21," *Cell*, 78:67–74 (1994).

Lloyd, R.V. et al., "Aberrant $p27^{kip1}$ Expression in Endocrine and Other Tumors," *American Journal of Pathology*, 150 (2):401–407 (1997).

Zhang, P. et al., "Cooperative Between the Cdk Inhibitors p27KIP1 and p57KIP2 in the Control of Tissue Growth and Development," *Genes & Development*, 12:3162–3167 (1998).

Someya, A.K. and Shioda, M., "The Possible Involvement of Replication–Related Proteins with a Dead–Box–Like Motif in Cell–Free DNA Replication of Xenopus Eggs," *Biochemical and Biophysical Research Communications*, 212(3):1098–1105 (1995).

McCafferty, J. et al., "Phage Antibodies: Filamentous Phage Displaying Antibody Variable Domains," *Nature*, 348:552–554 (1990).

Scholzen, T. and Gerdes, J., "The Ki–67 Protein: From the Known and the Unknown," *Journal of Cellular Physiology*, 182:311–322 (2000).

\* cited by examiner

MONOCLONAL ANTIBODIES AGAINST HUMAN PROTEIN MCM3, PROCESS FOR THEIR PRODUCTION, AND THEIR USE

RELATED APPLICATIONS

This application is the U.S. National Phase of International Application No. PCT/EP00/02910, filed Mar. 31, 2000, designating the United States and claiming priority under 35 U.S.C. §119 to German Application No. DE 199 15 057.5, filed Apr. 1, 1999.

DESCRIPTION

1. Technical Field

The present invention relates to monoclonal antibodies against human protein Mcm3, processes for their production and their use.

2. Prior Art

Mcm proteins were first described in the barm S. cerevisiae. It is known, that these proteins play an important role in the initiation of DNA replication, which was shown in the barm by its decisive role in the transmittance of extra chromosome DNA segments, minichromosomes (Maine et al., Genetics, 1984, 106:365–385). This feature was the basis for the naming for these proteins, minichromosome maintenance, Mcm. The proteins of the Mcm family are highly conserved with respect to evolution.

At present six proteins (Mcm2, Mcm3, Mcm4, Mcm5, Mcm6, Mcm7) are described in the human system which with other cell cycle dependent structures form a protein complex that is necessary for DNA replication, and which were already postulated as DNA replication licence factors by J. J. Blow and R. A. Laskey in 1988 (Nature, 332:546–548). Mcm3 protein plays an important role by forming a biochemical strong bond with Mcm5 (A. Richter, R. Knippers, Eur. J. Biochem., 1997, 247:136–141). Since Mcm3 and the other members of the Mcm family have such a basic function in the cell cycle, detection systems are desired, preferably immunobiochemical and immunohistological detections. Such detections are of need because new parameters for medical diagnosis, preferably in cancer diagnosis, can be achieved therewith.

It is known that human Mcm protein is immunogenic in the rabbit (Thommes et al., Nucleic Acid Res., 1992, 20:1069–1074). But the known polyclonal antisera either do not react monospecifically in immunobiochemical analyses (Western Blot) and/or are not applicable quickly and without problems in routine immunohistology (Hu, B., et al., Nucleic Acid Res., 1993, 21: 5289–5293). Therefore, there is no tool at hand that can serve as a detection method for Mcm3 in medical diagnosis.

SUMMARY OF THE INVENTION

The object of the present invention is therefore to provide means that detect quickly and monospecifically Mcm3 protein in biochemical and also in histological systems conducted alone or together in combination. This detection can be conducted alone or in combination with other known markers.

According to the invention this is achieved by a monoclonal antibody directed against Mcm3 protein and being applicable both in immunobiochemical and in immunohistochemical detection systems, whereby these detections can be conducted alone or in combination.

Further, hybridomas producing monoclonal antibodies according to the invention are disclosed.

Another aspect of the invention is the provision of diagnostic compositions and detection kits comprising the monoclonal antibody according to the present invention. Yet another aspect is the use of the monoclonal antibody according to the present invention for the detection of Mcm3 in a sample.

Moreover, processes are disclosed relating to the production of a monoclonal antibody and hybridoma, respectively, according to the present invention.

Finally, the present invention relates to pharmaceutical preparations and medicines containing the monoclonal antibody and the use of the monoclonal antibody for the preparation of a medicament for the treatment of certain diseases.

Also, within the scope of the invention are methods for treating diseases or disorders which are associated with an aberrant Mcm3 level or activity or which can benefit from modulation of the activity or level of Mcm3. The methods comprise administering, e.g., either locally or systemically to a subject, a pharmaceutically effective amount of a composition comprising an MCm3 antibody according to the present invention.

DETAILED DESCRIPTION OF THE INVENTION

According to the invention a monoclonal antibody directed against Mcm3 protein and being applicable both in immunobiochemical and in immunohistochemical detection systems, whereby these detections can be conducted alone or in combination is provided.

The monoclonal antibody according to the present invention can be obtained from any animal or the human being, whereby the monoclonal antibodies of the mouse are preferred.

Further, the monoclonal antibody may be altered biochemically, by genetic manipulation, or it maybe synthetic, with the antibody possibly lacking portions completely or in parts, said portions being necessary for the recognition of Mcm3 and being substituted by others imparting further advantageous properties to the antibody.

A hybridoma cell line producing a preferred monoclonal antibody of the present invention, namely, a monoclonal mouse antibody with said above-mentioned detection, was deposited at the Deutsche Sammlung von Mikroorganismen und Zellkulturen GmbH (DSMZ), Mascheroder Weg 1b, D-38124, Braunschweig, Germany under Accession No. DSM ACC2388 on Feb. 16, 1999.

The term "antibody" as used herein refers to immunoglobulin molecules and immunologically active portions of immunoglobulin molecules, i.e., molecules that contain an antigen binding site which specifically binds (immunoreacts with) Mcm3. Examples of immunologically active portions of immunoglobulin molecules include F(ab) and $F(ab')_2$ fragments which can be generated by treating the antibody with an enzyme such as pepsin. The invention provides monoclonal antibodies that bind Mcm3. The term "monoclonal antibody" or "monoclonal antibody composition", as used herein, refers to a population of antibody molecules that contain only one species of an antigen binding site capable of immunoreacting with a particular epitope of Mcm3. A monoclonal antibody composition thus typically displays a single binding affinity for Mcm3 with which it immunoreacts.

A disease, a disorder or condition "associated with" or "charterized by" an aberrant Mcm3 activity refers to a disease, disorder or condition in a subject which is caused by or contributed to by an aberrant Mcm3 activity.

The term "treating" as used herein is intended to encompass curing as well as ameliorating at least one symptom of the condition or disease.

Monoclonal anti-Mcm3 antibodies can be prepared by immunizing a suitable subject with an Mcm3 immunogen. An appropriate immunogenic preparation can contain, for example, recombinantly expressed Mcm3 protein or a chemically synthesized Mcm3 polypeptide. The preparation can further include an adjuvant, such as Freund's complete or incomplete adjuvant, or similar immunostimulatory agents. Immunization of a suitable subject with an immunogenic Mcm3 preparation induces an anti-Mcm3 antibody response.

The anti-Mcm3 antibody titer in the immunized subject can be monitored over time by standard techniques, such as with an enzyme linked immunosorbent assay (ELISA) using immobilized Mcm3. If desired, the antibody molecules directed against Mcm3 can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Koehler and Milstein (1975) Nature 256:495–497) (see also, Brown et al. (1981) J. Immunol. 127:539–46; Brown et al. (1980) J. Biol. Chem. 255:4980–83; Yeh et al. (1976) Proc. Natl. Acad. Sci. US.4 76:2997–3 1; and Yeh et al. (1982) Int. J. Cancer 29:269–75), the more recent human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing a monoclonal antibody hybridomas is well known (see generally R. H. Kenneth, in Monoclonal Antibodies: A new Dimension in Biological Analyses, Plenum Publishing Corp., New York, N.Y. (1980); E. A. Lerner (1981) Yale J: Biol. Med., 54:387402; M. L. Gefter et al. (1977) Somatic Cell Genet. 3:23136). Briefly, an immortal cell line (typically a myeloma) is fused to lymphocytes (typically splenocytes) from a mammal immunized with Mcm3 immunogen as described above, and the culture supernatants of the resulting hybridoma cells are screened to identify a hybridoma producing a monoclonal antibody that binds Mcm3.

Any of the many well known protocols used for fusing lymphocytes and immortalized cell lines can be applied for the purpose of generating anti-Mcm3 monoclonal antibodies (see, e.g., G. Galfre et al. (1977) Nature 266:55052; Gefter et al. Somatic Cell Genet., cited supra; Lerner, Yale J. Biol. Med, cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS 1/1-Ag4-1; P3×63-Ag8.653 or Sp2/O-Agl4 myeloma lines. Typically, HAT-sensitive mouse myeloma cells are fused to mouse splenocytes using polyethylene glycol ("PEG"). Hybridoma cells resulting from the fusion are then selected using HAT medium, which kills unfused myeloma cells (unfused splenocytes die after several days because they are not transformed). Hybridoma cells producing a monoclonal antibody of the invention are detected by screening the hybridoma culture supernatants for antibodies that bind Mcm3, e.g., using a standard ELISA assay.

Alternative to preparing monoclonal antibody-secreting hybridomas, a monoclonal anti-Mcm3 antibody can be identified and isolated by screening a recombinant combinatorial immunoglobulin library (e.g., an antibody phage display library) with Mcm3 to thereby isolate immunoglobulin library members that bind Mcm3. Kits for generating and screening phage display libraries are commercially available (e.g., the Pharmacia Recombinant Phage Antibody System, Catalog No. 27-9400-01; and the Stratagene SurfZAP® Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication. No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J 12:725–734; Hawkins et al. (1992) J. Mol. Biol. 226:889–896; Clarkson et al. (1991) Nature 352:624–628; Gram et al. (1992) Proc. Natl. Acad. Sci. USA 89:3576–3580; Garrad et al. (1991) Bio/Technology 9:1373–1377; Hoogenboom et al. (1991) J\tUC. Acid Res. 19:4133–4137; Barbas et al. (1991) Proc. Natl. Acad. Sci. USA 88:7978–7982; and McCafferty et al. Nature (1990) 348:552–554.

Additionally, recombinant anti-Mcm3 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,S67; Cabilly et al. European Patent Application 12 S,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80: 1553–1559); Morrison, S. L. (1985) Science 229: 1202–1207; Oi et al. (1986) Bio Techniques 4:214; Winter U.S. Pat. No. 5,225, 539; Jones et al. (1986) Nature 321:552–525; Verhoeyan et al. (1988) Science 239: 1534; and Seidler et al. (1988) J.

Immunol. 141:4053–4060. An anti-Mcm3 monoclonal antibody can be used to isolate Mcm3 by standard techniques, such as affinity chromatography or immunoprecipitation. An anti-Mcm3 antibody can be used to detect Mcm3 protein (e.g., in a cellular lysate or cell supernatant) in order to evaluate the abundance and pattern of expression of Mcm3. Anti-Mcm3 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, (-galactosidase, or acetylcholinesterase); examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, Cy-dyes, Alexa-dyes or phycoerythrin; an example of a luminescent material includes luminol; examples of bioluminescent materials include luciferase, luciferin, and aequorin, and examples of suitable radioactive material include $^{125}$I, $^{131}$I,; $^{35}$S or $^3$H.

Preferably, monoclonal antibodies according to the invention can be produced with the initial screening strategy described further below. Since a plurality of prepared hybridoma are either not monospecifically against Mcm3 protein or are applicable only in immunobiochemical detection systems but not in imunohistological systems and vice versa, initial examination of generated hybridoma cells requires this strategy to produce monoclonal antibodies according to the invention which have both properties.

For the production of genetically altered and/or synthetic antibodies having the properties according to the invention one can start e.g. from monoclonal antibodies obtained as described above. For this it is suitable to analyse the Mcm3 binding regions of the monoclonal antibodies and to identify the parts that are necessary and unnecessary for the detection described above. Then the necessary portions can be modified and the unnecessary portions can be eliminated completely or in part and can be substituted, respectively, by portions imparting further advantageous properties to the antibodies. Also, portions not within the binding regions of the antibodies can be modified, eliminated, or substituted. It is known by the skilled person that particularly the DNA recombination technology is suitable for the above measures.

Monoclonal antibodies according to the invention are distinguished by detecting Mcm3 monospecifically both in biochemical and histological detecting systems. The antibodies are therefore suitable for the fast detection of a Mcm3 expression in very different samples.

Within the present context, the term "sample" is intended to cover all types of samples suitable for the purpose of the invention. Examples of such samples are serum, sputum, urine, liquor, tissue, and biopsies. In particular the sample may be a blood sample or a gynaecological sample.

Because of these features the antibodies according to the invention are excellently suitable in the application of diagnostic problems, in which comparatively the tissue topological distribution analysis, e.g. determined by immunohistochemistry with quantitative expression parameters, e.g. obtained by Western Blot or immunoprecipitation, shall be analysed.

With the antibodies according to the invention the monospecific detection of the Mcm3 expression can be performed reliably in one-by-one conducted immunobiochemical detection methods such as ELISA, Western Blot, and immunoprecipitation, the Western Blot hereby being preferred, or immunohistochemical tissues, preferably on routine fixed and paraffin embedded tissue. For this the antibodies according to the invention may be labelled, if it is appropriate, as described above, or employed in combination with labelled antibodies directed against them or other reagents.

Monoclonal antibodies according to the invention can inhibit in vivo the assembly of DNA precursors and therefore inhibit cell proliferation. Thus, these antibodies or the above mentioned derivatives of the same are suitable for the therapy of states of a disease which are accompanied by raised cell proliferation. Examples of such diseases are tumours, allergies, autoimmune diseases, scar formation, inflammations and rheumatic diseases as well as the suppression of defense reactions of transplantations.

For the production of pharmaceutical composition or a medicine the monoclonal antibodies according to the invention can be used alone or combined with common carriers, adjuvants and/or additives. The antibodies are suitable for the systemic, local, subcutaneous, intrathecal and topical application and for application by enema. For this they can be applied solved in suitable solvents, preferably as aqueous solution, in the form of liposomes, as emulsion or in solid state, e.g. as powder or in the form of microcapsules.

Alternatively, a monoclonal antibody of the present invention can be administered in a combined method of treatment with a different pharmaceutically active agent. Pharmaceutically active agents, that can be formulated with the monoclonal antibodies of the present invention, or alternatively can be administered in a combined method of treatment, can be for instance antibodies, in particular monoclonal antibodies, against other antigens, thus providing a "cocktail" containing a monoclonal antibody of the present invention and one or more (monoclonal) antibodies against other antigens involved in the pathogenesis of the relevant disease state.

Further active agents, that can be formulated with the monoclonal antibodies of the present invention, or alternatively can be administered in a combined method of treatment, especially in order to produce a therapeutically useful effect, depend on the disease state to be cured and are, for instance, commercially available gamma globulin and immune globulin products, antibiotics, antimicrobial products, antibacterial and antitumor agents or a mixture of two or more of them.

Monoclonal antibodies according to the invention can be employed in a particularly advantageous way in the therapy of tumours, namely as such or in combination with other therapeuticals and forms of therapy respectively, such as radiation that is resistant against conventional tumour therapeuticals. Such resistances occur in unspecific cytostatica such as vinblastin or cisplatin either secondarily, i.e. after repeated application, or exist primarily at certain tumours, such as carcinoma of the kidneys.

The dosages of such antibodies will vary with the condition being treated and the recipient of the treatment, but will be in the range of 1 to about 100 mg for an adult patient preferably 1 to 10 mg usually administered daily for a certain period. A two part dosing regime may be preferable wherein 1 to 5 mg are administered.

In another preferred embodiment, the detection of Mcm3 is conducted in combination with the detection of the proteins Ki-67 and p27.

One of the most cited cell cycle associated proteins, used for histopathologic diagnostics within the past 16 years, is the Ki-67 protein (Scholzen T and Gerdes J (2000) J Cell Physiol 182: 311–322; Gerdes J, Schwab U, Lemke H and Stein H (1983). Int.J.Cancer 31, 13–20). The Ki-67 protein is expressed in proliferating cells, but rapidly disappears when cells enter a resting state (Baisch, H. and Gerdes, J (1987). Cell Tissue Kinet. 20(4), 387–391). Clinical studies have shown that the Ki-67 antigen is an independent prognostic marker in many different human neoplasms, e.g. breast cancer (Jansen R L, Hupperets P S, Arends J W, Joosten-Achjanie S R, Volovics A, Schouten H C, and Hillen H F (1998). Br. J. Cancer, 78: 460–465), soft tissue sarcoma, meningeomas (Perry A, Stafford S L, Scheithauer B W, Suman V J, and Lohse C M (1998). Cancer 82: 2262–2269), prostate cancer (Mashal R D, Lester S, Corless C, Richie J P, Chandra R, Propert K J, and Dutta A (1996) Cancer Res 56(18):4159–63) and non-Hodgkin lymphoma (Gerdes et al. (1984), J. Immunol. 133: 1710–1715).

The protein p27 belongs to the family of cyclin dependent kinase inhibitors (CDKI), which regulate cell cycle progression by binding and inactivating cyclin-dependent-kinases complexes at defined checkpoints within the cell cycle (Toyoshima H, and Hunter T (1994) Cell 78(1):67–74). The expression of p27 serves as a robust marker for differentiation in normal developing tissue and also in tumors displaying deregulated growth (Lloyd R V, Jin L, Qian X, and Kulig E (1997) Am J Path 150: 401–407., Zhang P, Wong C, DePinho R A, Harper J W, and Elledge S J (1998) Genes Dev 12(20):3162–3167).

Performing combined staining of tissues detecting the three proteins simultaneously, allow a more detained assessment of cell proliferation and differentiation processes that determine individual tumor growth Mcm3 protein is expressed in cells that have ceased to proliferate, but are not terminally differentiated according to the absence of p27 protein expression, whereas Ki-67 is expressed in proliferating cells only. P27 can be found in quiescent cells but not in proliferating cells. Ki-67, Mcm3 and p27 provide one set of parameters which define complementary biological properties that are suitable for a detailed characterization of disordered cell growth and tumorgenesis. Tumor diagnostics may also benefit from a combined assessment of these markers which may be of help to choose the most appropriate therapy concept for an individual patient.

The present invention will be illustrated by the following examples:

EXAMPLES

Example 1

Production of monoclonal antibodies according to the invention.

Mice were used for immunisation. Recombinant human Mcm3 protein was used as antigen.

Record of immunisation and fusion Day 1: 100 µg Mcm3 protein in 100 µl PBS (phosphate buffered saline) were mixed completely and thoroughly with 100 µl Freund's adjuvant and were injected subsequently into a mouse.

Day 14: 50 µg Mcm3 protein in 100 µl PBS were mixed completely and thoroughly with 100 µl Freund's adjuvant and were injected subsequently into a mouse.

Day 21: 50 µg Mcm3 protein in 100 µl PBS were mixed completely and thoroughly with 100 µl Freund's adjuvant and were injected subsequently into a mouse.

Day 37: 50 µg Mcm3 protein in 100 µl PBS were mixed completely and thoroughly with 100 µl Freund's adjuvant and were injected subsequently into a mouse.

On day 39 the mouse was killed painlessly. Spleen cells were removed and fused with myeloma cells. Hybridoma that reached full growth were obtained Screening of hybridoma supernatant and cloning.

At first supernatants of the hybridoma which reached full growth were tested in a spot-blot-assay. For this 1 ml recombinant human Mcm3 in PBS (2 ng/ml) was placed on. 1 cm×0.5 cm sized pieces of nitrocellulose membrane. These pieces are placed in a 48 well-plate and dried for 15 minutes at room temperature. Subsequently incubation was made with blocking puffer (PBS, 0.005 Tween 20, 4% gelatine) for 45 minutes at room temperature. After several washing steps with PBS (0.05% Tween 20, 0.5% gelatine) incubation was made with the hybridoma supernatant for 60 minutes at room temperature. After several washing steps with PBS (0.05% Tween 20, 0.5% gelatine) a commercially available phosphatase-coupled goat-anti-mouse antibody, Dianova, Hamburg (dilution according to the instruction of the producer 1:10000) was added. After incubation for 1 hour at room temperature with PBS (0.05% Tween 20, 0.5% gelatine) the alkaline phosphatase detection reaction was conducted with the developer solution (36 mM 5' bromo-4-chloro-3-indolylphosphate; 400 mM nitro blue tetrazolium, 100 mM Tris-HCl, pH 9.5, 100 mM NaCl, 5 mM $MgCl_2$) for 10 minutes at room temperature.

The hybridoma supernatant which were tested positive in the spot-blot were tested subsequently immunohistologically. For this paraffin sections, e.g. tonsil, were dehydrated according to standard procedures (2×100% xylene, 2×100% EtOH, 2×70% EtOH, 2×40% EtOH), followed by washing briefly in water. The sections were then cooked in citrate buffer pH 6 (2.1 g citric acid monohydrate for 1l, adjust with 2N NaOH to pH 6) in a pressure cooker for 1–5 minutes. After opening the cooker the sections were washed immediately in cold (RT) TBS, followed by incubation with hybridoma supernatant in a humid chamber for 30 minutes. After washing in TBS for several times antibodies bound to the sections were detected by means of the indirect immunoperoxidase method, stained with hemalum, embedded and evaluated microscopically.

The antibody according to the present invention shows the following staining pattern. The antibody predominantly reacts with the nuclei of cells in proliferative regions, indicated by the fact that cells of the dark zone within the germinal centers of human tonsils stain positive for Mcm3. Likewise cells near the basal layer of the normal mucosa react with the Mcm3 specific antibody. It should be noted that Mcm3 staining was also seen in the intermediate and upper layer which belong to the non-proliferating cell compartment of the oral mucosa.

Hybridoma which were positive both in the spot-blot and in immunohistology, were cloned and recloned until they were monoclonal. Independent monoclonal antibodies were obtained. A hybridoma cell producing a monoclonal antibody according to the invention was deposited at the Deutsche Sammlung von Microorganism und Zellkulturen GmbH (DSMZ), Mascheroder Weg 1b, D-38124, Braunschweig, Germany under Accession No. DSM ACC2388 on Feb. 16, 1999.

Example 2

Western Blot analysis of cell lysates with a polyclonal rabbit anti-Mcm3 antibody and a monoclonal antibody according to the invention.

Cell lysates of the cell line HELA (H) and CHO (C) were, applied to sodium dodecyl sulphate polyacrylamide gel electrophoresis (SDS PAGE). The proteins separated in the gel were transferred to a nitrocellulose membrane in a wet-blotting chamber over night. This membrane was then incubated with a diluted rabbit anti Mcm3 antiserum (Hu, B., et al., Nucleic Acid Res., 1993, 21: 5289–5293) (0.15 µg/ml ) for 1 hour at room temperature. After several washing steps with PBS (0.05% Tween 20, 0.5% gelatin) a commercially available phosphatase-coupled goat-rabbit antibody (dilution according to the instructions of the producer, Dianova, Hamburg 1:10000)was added. After incubation of 1 hour at room temperature and once more washing in TNT-buffer (150 mM NaCl, 10 mM Tris ph 7.5, 0.05% Tween 20) the detection was conducted with the chemiluminescence method with the ECL system (Amersham Life Science, Braunschweig) according to the instructions of the producer.

It turned out that the polyclonal anti-Mcm3 rabbit antibody revealed, besides the expected prominent main protein band with an apparent molecular weight of 105 kDa, further proteins in the molecular weight range between 50 kDa and 90 kDa.

The monoclonal anti-Mcm3 antibody according to the invention revealed only the expected protein band with an apparent molecular weight of 105 kDa.

Thus, it is clearly demonstrated by Western Blot analysis that the antibody according to the present invention recognises only one band while the polyclonal antibody detects further bands in the range of 90 to 50 kDa.

Further, in immunohistochemical studies, the monoclonal antibody according to the present invention demonstrates its usefulness for the detection of Mcm3

Example 3

Immunoprecipitation with anti Mcm3 antibodies according to the invention

1 µg anti-Mcm3 primary antibody is added to 10 µl Dyna-beads (Dynal M280 sheep-anti-mouse, Dynal, Hamburg) and incubated for 30 minutes at 4° C. under rolling.

Cell preparations (1×10$^6$ Cells) are taken up in immunoprecipitation buffer (18 mM Tris/HCl, 150 mM NaCl, 0.3% hexadecylmethyl-ammoniumbromide, 5 mM EDTA and 1 mM DTT) comprising protease inhibitors, cooked for 5 minutes, cooled on ice and centrifuged (5 minutes, 14000 rpm). The excess liquid is added to the complex of Dynalbeads/primary antibodies and incubated at 4° C. for 30 minutes on a roller.

Then the tube is placed in a Dynal magnetic concentrator for 20 seconds and the excess liquid is removed. Magnetic beads are resuspended in 500 µl NET (Tris/HCl 18 mM, NaCl 150 mM, EDTA 5 mM, DTT 1 mM) placed again in the magnetic concentrator and the supernatant is removed after 20 seconds. In this way, the beads are washed several times.

The so purified Mcm3 can then be analysed by means of SDS-PAGE.

Example 4

Micro injection of anti-Mcm3 antibodies according to the invention in nuclei of permanent cell line cells.

HEp-2 were cultivated on CELLocate® cover slips for microinjection and used in the logarithmic growth period. Anti-Mcm3 antibodies according to the invention and an irrelevant control antibody, respectively, were microinjected with a transjector and micro manipulator into the nuclei under light microscopy control (pressure of injection 130 hPa; time of injection between 0.3 and 0.5 seconds). The injected cells were then cultivated with bromodesoxyuridin (BrdU) containing (0.1 mM) medium for 6 hours. After fixation (5 minutes 4% paraformaldehyde at room temperature) the cover slips were washed three times in Tris-buffered saline (TBS), incubated in 100% EtOH for 10 minutes at −20° C. followed by permeation of the adhering cells by transferring directly in 0.1% Triton X-100 TBS for 10 minutes by room temperature. The injected antibodies were then detected with a commercially available Cy3 coupled goat anti mouse antibody, Dianova, Hamburg (dilution according to the instructions of the producer in PBS/10% bovine serum albumin). The preparations were first incubated in 2M HCl for 60 minutes at 37° C. for the detection of BrdU fixed into the cells. Subsequently, the preparations were washed first several times with distilled water, then two times with PBS. Then incubation with a commercially available FITC labelled anti BrdU antibody, Boehringer Mannheim, Mannheim (dilution according to the instructions of the producer) overnight at 4° C. in a humid chamber was performed. Then the preparations were washed thoroughly five times in PBS for 10 minutes, covered with DABCO (1,4-diazabicyclo[2,2,2]octane) in 90% glycerol, and evaluated by fluorescence microscopy.

It turned out that almost all cells injected with control antibodies incorporated also BrdU, hence passing during the experiment the normal cell cycle. In contrast only between 20% to 50% of the cells that had been injected with anti-Mcm3 antibodies according to the invention incorporated BrdU. The proliferation of these cells was therefore inhibited by the antibodies according to the invention.

REFERENCES

1. Maine et al., Genetics, 1984, 106:365–385
2. J. J. Blow and R. A. Laskey, Nature, 1988, 332:546–548
3. A. Richter, R. Knippers, Eur. J. Biochem., 1997, 247:136–141
4. Thommes et al., Nucleic Acid Res., 1992, 20:1069–1074
5. Hu, B., et al., Nucleic Acid Res., 1993, 21: 5289–5293
6. Koehler and Milstein, Nature, 1975, 256:495–497
7. Brown et al., J. Immunol., 1981, 127:539–46 (1981)
8. Brown et al., J. Biol. Chem., 1980, 255:4980–83
9. Yeh et al., Proc. Natl. Acad. Sci. US.4 76:2997–3 1 (1976)
10. Yeh et al., Int. J. Cancer, 1982, 29:269–75
11. Kozbor et al. Immunol Today, 1983, 4:72
12. Cole et al. (1985), Monoclonal Antibodies and Cancer Therapy, Alan R. Liss, Inc., pp. 77–96
13. R. H. Kenneth, in Monoclonal Antibodies: A new Dimension in Biological Analyses, Plenum Publishing Corp., New York, N.Y. (1980)
14. E. A. Lerner, Yale J: Biol. Med., 1981, 54:387402
15. M. L. Gefter et al., Somatic Cell Genet., 1977, 3
16. G. Galfre et al., Nature, 1977, 266:55052
17. Ladner et al., U.S. Pat. No. 5,223,409
18. Kang et al. PCT International Publication No. WO 92/18619
19. Dower et al., PCT International Publication No. WO 91/17271
20. Winter et al., PCT International Publication WO 92/20791
21. Markland et al., PCT International Publication No. Wo 92/15679
22. Breitling et al., PCT International Publication WO 93/01288
23. McCafferty et al. PCT International Publication No. WO 92/01047

24. Garrard et al. PCT International Publication No. WO 92/09690
25. Ladner et al. PCT International Publication No. WO 90/02809
26. Fuchs et al., Bio/Technology, 1991, 9:1370–1372
27. Hay et al., Hum. Antibod. Hybridomas, 1992, 3:81–85
28. Huse et al., Science, 1989, 246:1275–1281
29. Griffiths et al., EMBO J, 1993, 12:725–734
30. Hawkins et al., J. Mol. Biol., 1992, 226:889–896
31. Clarkson et al., Nature, 1991, 352:624–628
33. Gram et al., Proc. Natl. Acad. Sci. USA, 1992, 89:35763580
34. Garrad et al., Bio/Technology, 1991, 9:1373–1377
35. Hoogenboom et al., J\tUC. Acid Res., 1991, 19:4133–4137
36. Barbas et al., Proc. Natl. Acad. Sci. USA 1991, 88:7978–7982
37. McCafferty et al., Nature, 1990, 348:552–554
38. Robinson et al. International Application No. PCT/US86/02269
39. Akira, et al. European Patent Application 184,187
40. Taniguchi, M., European Patent Application 171,496
41. Morrison et al. European Patent Application 173,494
42. Neuberger et al. PCT International Publication No. WO 86/01533
43. Cabilly et al. U.S. Pat. No. 4,816,S67
44. Cabilly et al. European Patent Application 12 S,023
45. Better et al., Science, 1988, 240:1041–1043
46. Liu et al., Proc. Natl Acad. Sci. USA, 1987, 84:3439–3443
47. Liu et al., J. Immunol., 1987, 139:3521–3526
48. Sun et al., Proc. Natl. Acad. Sci. USA, 1987, 84:214–218
49. Nishimura et al., Canc. Res., 1987, 47:999–1005
50. Wood et al., Nature, 1985, 314:446–449
51. Shaw et al., J. Natl. Cancer Inst., 1988, 80: 1553–1559)
52. Morrison, S. L., Science, 1985, 229: 1202–1207
53. Oi et al., Bio Techniques 1986, 4:214
54. Winter U.S. Pat. No. 5,225,539
55. Jones et al., Nature, 1986, 321:552–525
56. Verhoeyan et al., Science, 1988, 239: 1534
57. Seidler et al., J. Immunol., 1988, 141:4053–4060
58. Scholzen T and Gerdes J, J Cell Physiol, 2000, 182: 311–322
59. Gerdes J, Schwab U, Lemke H and Stein H, Int.J.Cancer, 1983, 31, 13–20
60. Baisch, H, and Gerdes, J, Cell Tissue Kinet., 1987, 20(4), 387–391
61. Mashal R D, Lester S, Corless C, Richie J P, Chandra R, Propert K J, and Dutta A, Cancer Res, 1996, 56(18): 4159–63
62. Toyoshima H, and Hunter T, Cell, 1994, 78(1):67–74
63. Lloyd R V, Jin L, Qian X, and Kulig E, Am J Path 1997, 150: 401–407
64. Zhang P. Wong C, DePinho R A, Harper J W, and Elledge S J, Genes Dev. 1998, 12(20):3162–3167.

What is claimed is:

1. A monoclonal antibody detecting and binding monospecifically human Mcm3 both immunohistologically and immunobiochemically, whereby the epitope of the monoclonal antibody of the hybridoma cell line with the deposit number DSM ACC2388.

2. A monoclonal antibody specific for human Mcm3 which is produced by the hybridoma cell line with the deposit number DSM ACC2388.

3. A hybridoma cell line which expresses a monoclonal antibody specific for human Mcm3, whereby the hybridoma cell line is the cell line with the deposit number DSM ACC2388.

4. A diagnostic composition comprising a monoclonal antibody according to claim 1.

5. A diagnostic composition comprising a monoclonal antibody according to claim 2.

6. A diagnostic kit comprising the monoclonal antibody according to claim 1.

7. A diagnostic kit according to claim 6 for the combined detection of the expression of Mcm3, Ki-67 and p27 for tumor diagnosis.

8. A diagnostic kit comprising the monoclonal antibody according to claim 2.

9. A diagnostic kit according to claim 7 for the combined detection of the expression of Mcm3, Ki-67 and p27 for tumor diagnosis.

10. A method of detecting human Mcm3 using the monoclonal antibody of claim 1.

11. A method for the immunohistological, immunocytological or immunobiochemical detection of human Mcm3 in a sample using the monoclonal antibody of claim 1.

12. A method of claim 11 wherein the sample is selected from serum, sputum, urine, or liquor.

13. A method of claim 11 wherein the sample is tissue or a fine needle aspiration product.

14. A method of claim 11 wherein the method is an immunobiochemical method selected from ELISA, RIA, Western Blot, Far Western Blot, immunoprecipitation and affinity chromatographic steps.

15. A method of claim 11 wherein the method is an immunocytological method selected from FACS and MACS.

16. A method of claim 11 wherein the method is an immunohistological method selected from fluorescence, radioactive, enzymatic and chemiluminescence methods.

17. A process for the production of purified human Mcm3, characterized in that the process comprises an affinity chromatography step with a monoclonal antibody according to claim 1.

18. A process for the production of purified human Mcm3 comprising an immunoprecipitation step with a monoclonal antibody according to claim 1.

19. A method of detecting human Mcm3 using the monoclonal antibody of claim 2.

20. A method for the immunohistological, immunocytological or immunobiochemical detection of human Mcm3 in a sample using the monoclonal antibody of claim 2.

21. A method of claim 20 wherein the sample is selected from serum, sputum, urine, or liquor.

22. A method of claim 20 wherein the sample is tissue or a fine needle aspiration product.

23. A method of claim 20 wherein the method is an immunobiochemical method selected from ELSA, RIA, Western Blot, Far Western Blot, immunoprecipitation and affinity chromatographic steps.

24. A method of claim 20 wherein the method is an immunocytological method selected from FACS and MACS.

25. A method of claim 20 wherein the method is an immunohistological method selected from fluorescence, radioactive, enzymatic and chemiluminescence methods.

26. A process for the production of purified human Mcm3, characterized in that the process comprises an affinity chromatography step with a monoclonal antibody according to claim 2.

27. A process for the production of purified human Mcm3 comprising an immunoprecipitation step with a monoclonal antibody according to claim 2.

* * * * *